United States Patent [19]

Heimlich

[11] 4,323,078
[45] Apr. 6, 1982

[54] COLLAPSIBLE RESPIRATORY EXERCISER

[76] Inventor: Henry J. Heimlich, 17 Elmhurst Pl., Cincinnati, Ohio 45208

[21] Appl. No.: 177,988

[22] Filed: Aug. 14, 1980

[51] Int. Cl.$^3$ .......................... A61B 5/08; A63B 23/00
[52] U.S. Cl. ........................................ 128/728; 272/99
[58] Field of Search ............... 128/728, 725, 727, 730, 128/205.16; 272/99

[56] References Cited

U.S. PATENT DOCUMENTS

| | | | |
|---|---|---|---|
| 225,710 | 3/1880 | Marsh | 128/728 |
| 3,316,903 | 5/1967 | Richards | 128/205.16 |
| 3,467,078 | 9/1969 | Bird et al. | 128/728 |
| 4,096,855 | 6/1978 | Flemn | 272/99 X |
| 4,241,740 | 12/1980 | Brown | 272/99 X |

FOREIGN PATENT DOCUMENTS 436569  8/1912  France ............................ 128/728

Primary Examiner—Robert W. Michell
Assistant Examiner—John E. Hanley
Attorney, Agent, or Firm—Frost & Jacobs

[57] ABSTRACT

A collapsible respiratory exercising device for measuring the volume of air inhaled by the user. The device comprises a rigid upper plate, an orifice through the plate, an inhalation tube connected to the orifice, a tubular bellows attached beneath the plate and in communication with the orifice and tube, a lower plate attached to the lowermost end of the bellows which has sufficient mass to cause the bellows to fully expand, and measuring means with calibrated indicia attached to the upper plate for determining the change in volume of the bellows after inhalation, thereby indicating the amount of air that has been inhaled.

6 Claims, 3 Drawing Figures

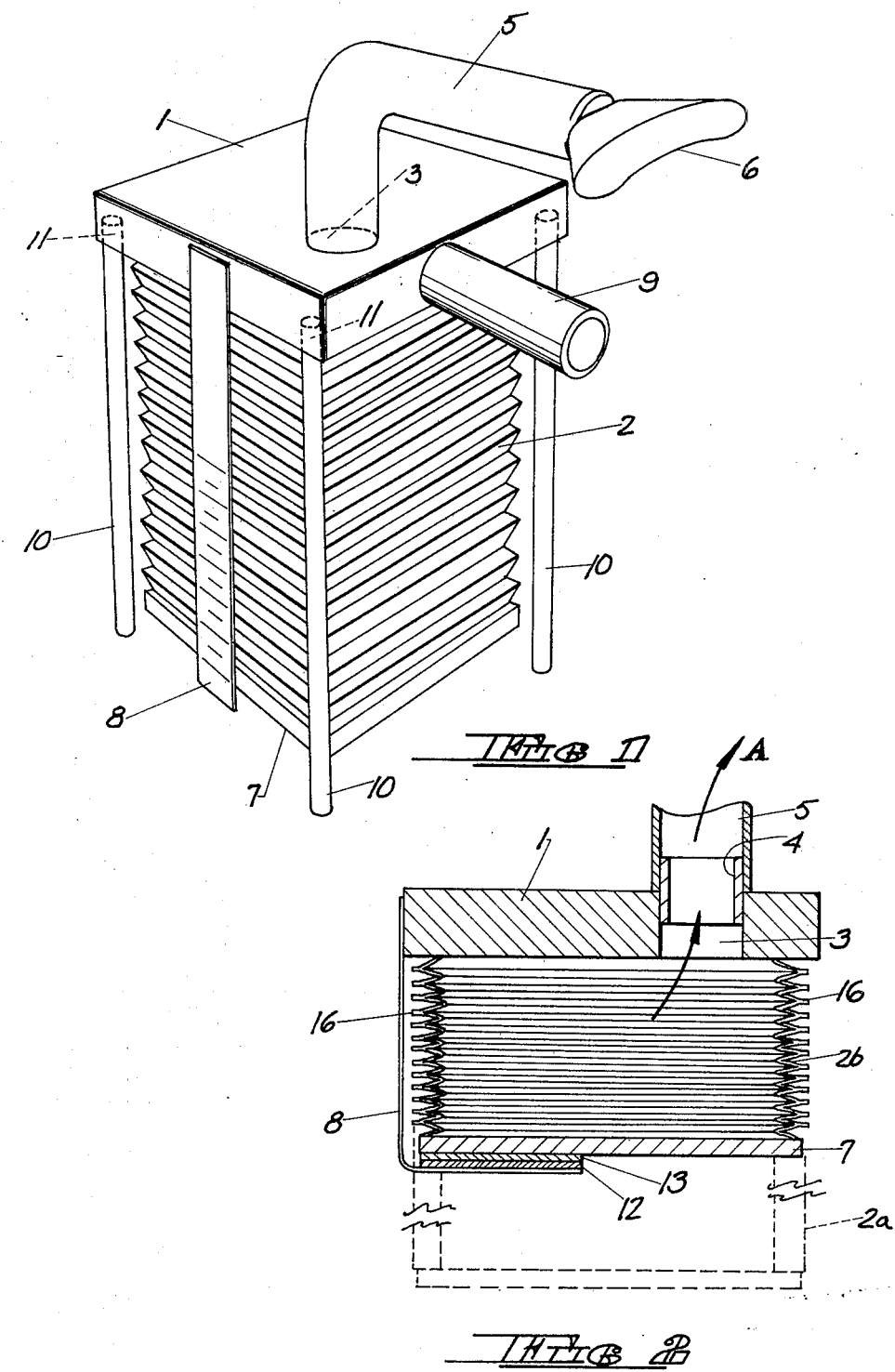

COLLAPSIBLE RESPIRATORY EXERCISER

BACKGROUND OF THE INVENTION

1. Field of the Invention

This invention relates to a respiratory exercising device and more particularly to a collapsible, compact deep breathing exerciser which induces hyperinhalation of the user's lungs.

2. Description of the Prior Art

Scientific studies have shown that expansion of the lungs through inspiration is extremely important in preventing or overcoming post-operative pneumonia and atalectasis. Several devices have been developed for single patient use to encourage proper expansion of the user's lungs. Devices of this nature are generally referred to as incentive spirometers or incentive deep-breathing exercisers, exemplary devices being disclosed in U.S. Pat. Nos. 4,037,836 and 4,060,074. These devices comprise one or more vertically disposed chambers, the chambers each containing a lightweight ball which is caused to rise as the user inhales through a flexible inhalation tube connected to the chambers. Alternatively, a lightweight piston fitted within a chamber can be made to move upwardly by withdrawing air from the chamber. Such devices measure the rate of air flow, i.e., air flow per second, to indicate what the user is accomplishing in terms of lung expansion.

However, researchers have determined that the rate of air flow is not the most accurate standard for determining actual lung expansion. By inhaling suddenly, a rapid air flow is achieved without properly expanding the lungs. Consequently, it is generally recommended that the patient's lungs be slowly and fully expanded by inspiration. Thus, the volume of air inhaled indicates the actual expansion of the lungs and is the proper criteria for determining the effectiveness of the exercise. It is therefore desirable to provide a device which will encourage optimum lung expansion and provide a visual measurement of the volume of air inhaled; thereby providing an accurate indication of the extent to which the lungs have been expanded.

In addition, devices of the prior art tend to be cumbersome and expensive. Since the user is often a bedridden individual, a lightweight, easily managed device is highly desirable, as is the ability to easily store the device when not in use. It is also highly desirable to provide a device which is of simple and inexpensive construction which can be produced at relatively low cost.

SUMMARY OF THE INVENTION

The collapsible respiratory exerciser of the present invention is designed to meet the recommendation that the patient's lungs be slowly and fully expanded; and fill the need for a compact, lightweight and inexpensive unit. To accomplish this, a tubular bellows is attached at one end to the undersurface of a rigid upper plate. A flexible inhalation tube communicates with the bellows through an orifice in the upper plate. The bellows is normally expanded to its fully extended condition prior to each use by a lower plate attached to the bottom end of the bellows; the lower plate acting as a weight. During use the bellows is effectively sealed from outside air by the upper and lower plates so that only the air contained within the bellows is withdrawn by the user.

By the very nature of a bellows, as air is withdrawn the bellows will contract and the weighted bottom will rise vertically in proportion to the volume of air withdrawn. A measuring means with calibrated indicia attached to the upper plate gives a visual indication of the volume of air inhaled. At the end of inhalation, the bellows may be maintained in its contracted position by preventing air from re-entering the bellows or by temporarily mechanically restraining the bellows, allowing the user ample time to determine the volume of air inhaled.

Although primarily intended for post-operative use, the invention can be used by singers and athletes or any other individuals interested in improving their respiratory expansion. The device will enhance proper breathing and increase lung capacity providing for better air exchange. The device also will be useful to persons suffering from emphysema.

BRIEF DESCRIPTION OF THE DRAWINGS

FIG. 1 is a perspective view of the collapsible respiratory exercising device.

FIG. 2 is a vertical sectional view of the device in the contracted state.

DETAILED DESCRIPTION

Figure 3:
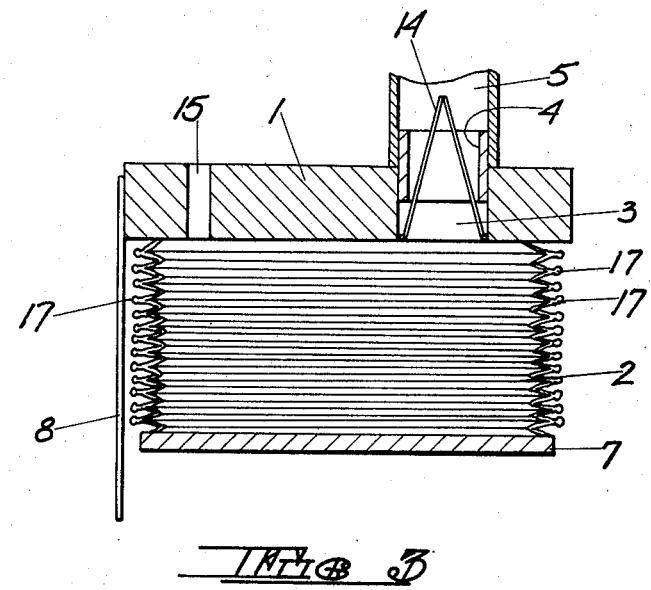
FIG. 3 is a fragmentary vertical sectional view illustrating the use of a one-way valve in the inhalation tube.

As shown in FIGS. 1 and 2, the collapsible exercising device comprises a rigid upper plate 1, preferably formed from plastic or other light weight material, to the under surface of which is attached a tubular bellows 2. The bellows 2 is preferably fabricated from a flexible non-fibrous film. In the embodiment illustrated the upper plate 1 is essentially square and the bellows 2 is correspondingly square in cross-section, although other configurations may be employed. For example, the plate can be circular and the bellows cylindrical. An orifice 3 extends through the upper plate 1 in communication with the bellows 2. A sleeve-like fitting 4 adapts the orifice 3 to receive a conventional flexible inhalation tube 5 having a mouthpiece 6. Alternatively, the end of the inhalation tube 5 may be press fitted directly into the orifice 3.

The lowermost end of bellows 2 is closed by the lower plate 7, which also may comprise a piece of plastic of a size to correspond to the cross-section dimensions of the bellows, the lower plate 7 being of sufficient mass to extend the bellows 2 to its fully expanded position without creating undue resistance to contraction.

Displacement of the bellows 2 is measured by a measuring means 8 having calibrated indicia thereon to indicate the volume of air displaced. The measuring means 8 may comprise a flexible tape suspended externally from a side edge of upper plate 1, as shown in FIG. 1, or it may be placed internally of the bellows, if the bellows is formed from transparent material.

To facilitate handling of the device by the user, a handle 9 preferably detachable, may be connected to upper plate 1 in any known manner. The device also may be provided with a stand, such as a series of detachable legs 10 of sufficient length to allow full expansion of the bellows and having their upper ends snuggly but releasably received by sockets 11 in upper plate 1, thereby enabling the user to place the device on a supporting surface.

In using the device, the patient inhales through the mouthpiece 6, thereby withdrawing air from the bellows 2, as indicated by arrow A. Since no outside air can enter the bellows during inhalation, a pressure gradient is created. The pressure of the ambient air is greater than that of the air with the bellows causing the bellows 2 to move from its expanded position, as indicated in FIG. 2 by the dotted lines 2a, to a contracted position 2b. By blocking the inhalation tube 5 and not allowing air to re-enter the bellows 2 at the end of inhalation, the bellows 2 will remain in a contracted position and the volume of air withdrawn can be readily determined using measuring means 8. Alternatively, means may be provided to temporarily restrain the bellows 2 in its contracted position. For example, and as shown in FIG. 2, the measuring means 8 in the form of a flexible tape may be used to secure the bellows in its contracted position, the tape being provided on its inner surface with a first portion 12 of a self-adhering fastener, such as a Velcro type fastener, the coacting portion 13 of the fastener being secured to the under surface of the lower plate 7. Alternatively, adjustable stop means can be provided on one of the legs 10 to retain the bellows in its contracted position. Thus, it is possible to obtain a sustained visual indication by the calibrated indicia on measuring means 8 of the volume of air which has been inhaled; the volume of air inhaled equalling the volume withdrawn from the bellows.

FIG. 3 illustrates a modification of the device wherein a one-way valve, such as flutter valve 14, is oriented to permit air to be withdrawn through inhalation tube 5, while preventing air from flowing back into the bellows through the inhalation tube 5. For this modification the upper plate 1 has a second orifice 15 communicating with the outside air. During inhalation the second orifice 15 is closed by a finger or suitable cap. With this design, the bellows will remain in its contracted position after inhalation as long as the second orifice 15 remains closed, since the flutter valve 14 serves to block the entry of air through the inhalation tube 5. Thus, upon completion of inhalation, the bellows can be maintained in the contracted position until the measurement is read, simply by holding a finger on the second orifice 15. When orifice 15 is opened, outside air will re-enter the bellows 2 through orifice 15 and the lower plate 7 will cause the bellows 2 to fully expand to its initial position of use.

In order to prevent possible inward collapse of the walls of the bellows 2, the edges or fold lines of the bellows may be provided with heat sealed fins, indicated at 16 in FIG. 2, which will reinforce the bellows and resist inward collapse. Alternately, the folding edges may be reinforced and strengthened by edge beading as seen at 17 in FIG. 3.

As should now be apparent, the invention provides a compact, lightweight, inexpensive respiratory exerciser which measures the volume of air inhaled by the user without regard to the rate of inhalation. By its construction the invention can be easily disassembled and stored in a convenient package.

Variations and modifications can be made without departing from the spirit and purpose of the invention.

I claim:

1. A collapsible respiratory exercising device consisting essentially of:
    an upper plate having an orifice extending therethrough;
    an inhalation tube detachably connected to said orifice;
    a flexible tubular bellows attached to and suspended from said upper plate, said plate closing the upper end of said bellows with said opening in communication with said bellows;
    a lower plate attached to and closing the lowermost end of said bellows, said lower plate having sufficient mass to fully expand said bellows and constituting the sole means for expanding said bellows; and
    a flexible tape suspended from said upper plate externally of said bellows, said tape having calibrated indicia thereon for measuring the extent to which said bellows has been contracted upon inhalation by a user, and attachment means on said tape engagable with said lower plate, whereby said tape may be wrapped around and secured to said lower plate to restrain said bellows in a contracted position.

2. The device recited in claim 1 wherein said bellows is made of a transparent material.

3. The device recited in claim 1 including support means adapted to be detachably secured to said upper plate, said support means being of a length such that the device may stand upright on a supporting surface with the bellows extended.

4. The device recited in claim 1 including detachable handle means connected to said upper plate to facilitate grasping the device during use and which may be removed for storage of the device.

5. The device recited in claim 1 including a one-way valve in said inhalation tube oriented to permit air to be withdrawn from said tube, and a second orifice through said upper plate in communication with said bellows.

6. The device as recited in claim 5 wherein said one-way valve is a flutter valve.

* * * * *